(12) United States Patent
McAnally

(10) Patent No.: US 9,354,097 B2
(45) Date of Patent: May 31, 2016

(54) SYSTEM, METHOD, AND COMPUTER PROGRAM PRODUCT FOR GENERATING A DRIVE SIGNAL IN A VIBRATING MEASURING DEVICE

(75) Inventor: Craig B. McAnally, Thornton, CO (US)

(73) Assignee: Micro Motion, Inc., Boulder, CO (US)

( * ) Notice: Subject to any disclaimer, the term of this patent is extended or adjusted under 35 U.S.C. 154(b) by 363 days.

(21) Appl. No.: 12/996,926

(22) PCT Filed: Jul. 1, 2008

(86) PCT No.: PCT/US2008/068928
§ 371 (c)(1),
(2), (4) Date: Dec. 8, 2010

(87) PCT Pub. No.: WO2010/002401
PCT Pub. Date: Jan. 7, 2010

(65) Prior Publication Data
US 2011/0098945 A1    Apr. 28, 2011

(51) Int. Cl.
*G01F 1/20*    (2006.01)
*G01F 1/05*    (2006.01)
(Continued)

(52) U.S. Cl.
CPC ............... *G01F 1/8436* (2013.01); *G01N 9/32* (2013.01)

(58) Field of Classification Search
CPC ......................................................... G01F 1/84

USPC .................. 702/45, 48, 50, 54, 56; 73/861.87
See application file for complete search history.

(56) References Cited

U.S. PATENT DOCUMENTS 5,555,190 A    9/1996 Derby et al.
6,360,175 B1 *    3/2002 Cunningham et al. .......... 702/56
(Continued)

FOREIGN PATENT DOCUMENTS

EP    0222503 A1    5/1987
EP    0816807 A2    7/1998
(Continued)

OTHER PUBLICATIONS

Machine translation of JP 07-286880.*
(Continued)

*Primary Examiner* — Gregory J Toatley
*Assistant Examiner* — Felix Suarez
(74) *Attorney, Agent, or Firm* — The Ollila Law Group LLC

(57) ABSTRACT

The present invention relates to a system, method, and computer program product for generating a drive signal for a vibrating measuring device (5). A drive chain ($C_1, C_2, C_3, C_N$) is selected from at least two drive chains ($C_1, C_2, C_3, C_N$). Each drive chain ($C_1, C_2, C_3, C_N$) modifies at least one pick-off signal to generate the drive signal. Each drive chain ($C_1, C_2, C_3, C_N$) generates a different mode of vibration in the at least one conduit (103A). The drive signal generated by the selected drive chain ($C_1, C_2, C_3, C_N$) is provided to a drive (104) of the vibrating measuring device (5).

27 Claims, 2 Drawing Sheets

(51) Int. Cl.
*G01F 1/56* (2006.01)
*G01F 1/86* (2006.01)
*G01F 1/84* (2006.01)
*G01N 9/32* (2006.01)

(56) References Cited

U.S. PATENT DOCUMENTS

| | | | | |
|---|---|---|---|---|
| 6,754,594 | B2 * | 6/2004 | Henry et al. | 702/45 |
| 7,505,854 | B2 * | 3/2009 | Henry et al. | 702/45 |
| 7,983,855 | B2 * | 7/2011 | Cunningham et al. | 702/45 |
| 8,017,858 | B2 * | 9/2011 | Mann | 84/742 |

FOREIGN PATENT DOCUMENTS

| | | | |
|---|---|---|---|
| EP | 1109016 | A2 | 6/2001 |
| JP | 07-286880 | | 10/1995 |
| JP | 07286880 | A * | 10/1995 |
| JP | 3658322 | B2 | 1/2004 |
| RU | 2155325 | C2 | 8/2000 |
| RU | 2241209 | C2 | 11/2007 |
| WO | 9807009 | A1 | 2/1998 |
| WO | 9928708 | A1 | 6/1999 |
| WO | 9944018 | A1 | 9/1999 |
| WO | 0101084 | A1 | 1/2001 |

OTHER PUBLICATIONS

V.V. Shahildyan and A.A. Lyakhovkina, "Phase Locked Loop", Moscow "Sviaz", 1966, total 335 pages, (p. 281 line 24-p. 282 line 26 and pp. 303-309.

* cited by examiner

SYSTEM, METHOD, AND COMPUTER PROGRAM PRODUCT FOR GENERATING A DRIVE SIGNAL IN A VIBRATING MEASURING DEVICE

FIELD OF THE INVENTION

The present invention relates to a system, method, and computer program product for generating a drive signal in a vibrating measuring device.

BACKGROUND OF THE INVENTION

Vibrating measuring devices such as, for example, densitometers and Coriolis flow meters are used for measuring a characteristic of flowing substances, such as, for example, density, mass flow rate, volume flow rate, totalized mass flow, temperature, and other information. Vibrating measuring devices include one or more conduits, which may have a variety of shapes, such as, for example, straight, U-shaped, or irregular configurations.

The one or more conduits have a set of natural vibration modes, including, for example, simple bending, torsional, radial, and coupled modes. At least one drive vibrates or drives the one or more conduits at a resonance frequency in one of these drive modes for purposes of determining a characteristic of the flowing substance. One or more electronics transmit a sinusoidal or a square wave drive signal to the at least one drive, which is typically a magnet/coil combination, with the magnet typically being affixed to the conduit and the coil being affixed to a mounting structure or to another conduit. The drive signal causes the drive to vibrate the one or more conduits at the drive frequency in the drive mode. For example, the drive signal may be a periodic electrical current transmitted to the coil.

At least one pick-off detects the motion of the conduit(s) and generates a sinusoidal pick-off signal representative of the motion of the vibrating conduit(s). The pick-off is typically a magnet/coil combination, with the magnet typically being affixed to one conduit and the coil being affixed to a mounting structure or to another conduit. The pick-off signal is transmitted to the one or more electronics; and according to well known principals the pick-off signal may be used by the one or more electronics to determine a characteristic of the flowing substance or adjust the drive signal, if necessary.

In order to drive a vibrating measuring device in a desired mode, a drive chain is typically employed. The drive chain modifies one or more pick-off signals to generate the drive signal. The drive chain reinforces the appropriate drive frequency and suppresses other drive frequencies. By way of an example, a generated drive signal may start with a pick-off signal. This pick-off signal may then be modified, for example, filtering out undesired modes, adjusting for signal gain, and phase shifting, to provide the generated drive signal.

Depending on operating conditions, a given vibrating measuring device may operate more accurately at certain frequencies. For example, certain vibrating measuring devices are capable of operating at either a low frequency first bend drive mode or a high frequency second bend drive mode. The low frequency first bend drive mode may provide better entrained air performance and the high frequency second bend drive mode may provide more accurate measurements across a wider range of operating conditions.

In situations where vibrating measuring devices are designed to operate in multiple modes, as a practical matter, it has been difficult to switch between modes because a single fixed drive chain is not capable of generating more than one mode. This is particularly problematic where any analog hardware, due to its fixed nature, is included as a component of the drive chain.

The present invention is directed to overcoming this disadvantage inherent in prior single conduit systems.

SUMMARY OF THE INVENTION

The scope of the present invention is defined solely by the appended claims, and is not affected to any degree by the statements within this summary.

According to one embodiment of the present invention, a system for generating a drive signal in a vibrating measuring device comprises at least one conduit, at least one drive, at least one pick-off, and one or more electronics. The at least one conduit is configured to receive a flowing substance. The at least one drive vibrates the at least one conduit. The at least one pick-off measures the motion of the at least one conduit. The one or more electronics includes at least two drive chains, wherein each drive chain modifies at least one pick-off signal to generate a drive signal used to vibrate the at least one conduit and each drive chain generates a different mode of vibration in the at least one conduit. The one or more electronics including a drive chain selector for selecting a drive chain from the at least two drive chains. The one or more electronics providing to the drive the drive signal generated by the selected drive chain.

According to embodiment of the present invention, a method for generating a drive signal for a vibrating measuring device that includes at least one conduit configured to receive a flowing substance, at least one drive that vibrates the at least one conduit, and at least one pick-off that measures motion of the at least one conduit, comprises the steps of providing one or more electronics with at least two drive chains, wherein each drive chain modifies at least one pick-off signal to generate the drive signal and each drive chain generates a different mode of vibration in the at least one conduit, selecting a drive chain from the at least two drive chains, and providing the drive signal generated by the selected drive chain to the drive.

According to another embodiment of the present invention, a computer program product is provided that comprises computer usable medium including executable code for executing a process for generating a drive signal for a vibrating measuring device (5), the process comprising selecting a drive chain from at least two drive chains, wherein each drive chain modifies at least one pick-off signal to generate the drive signal and each drive chain generates a different mode of vibration in the at least one conduit and providing the drive signal generated by the selected drive chain to a drive.

ASPECTS

According to one aspect of the present invention, a system for generating a drive signal in a vibrating measuring device comprises:

at least one conduit configured to receive a flowing substance;

at least one drive that vibrates the at least one conduit;

at least one pick-off that measures motion of the at least one conduit;

one or more electronics including at least two drive chains, wherein:

each drive chain modifies at least one pick-off signal to generate a drive signal used to vibrate the at least one conduit;

each drive chain generates a different mode of vibration in the at least one conduit;

the one or more electronics including a drive chain selector for selecting a drive chain from the at least two drive chains; and the one or more electronics providing to the drive the drive signal generated by the selected drive chain.

Preferably, each drive chain modifies at least one pick-off signal in a manner that reinforces a particular drive frequency and suppresses other drive frequencies.

Preferably, each drive chain includes a filter that filters out undesired modes of vibration.

Preferably, each drive chain includes a phase shift algorithm.

Preferably, each drive chain includes a gain adjusting algorithm.

Preferably, a user or program selects the drive chain.

Preferably, the drive chain) is selected according to whether entrained gas is present in the flowing substance.

Preferably, the drive chain is selected according to the noise of the pick-off signals.

Preferably, the drive chain is selected by accessing a look up table that correlates a variety of conditions to particular drive chains.

According to another aspect of the present invention, a method for generating a drive signal for a vibrating measuring device, including at least one conduit configured to receive a flowing substance, at least one drive that vibrates the at least one conduit, and at least one pick-off that measures motion of the at least one conduit, comprises the steps of:

providing one or more electronics with at least two drive chains, wherein:

each drive chain modifies at least one pick-off signal to generate the drive signal;

each drive chain generates a different mode of vibration in the at least one conduit;

selecting a drive chain from the at least two drive chains; and providing the drive signal generated by the selected drive chain to the drive.

Preferably, each drive chain modifies at least one pick-off signal in a manner that reinforces a particular drive frequency and suppresses other drive frequencies.

Preferably, each drive chain includes a filter that filters out undesired modes of vibration.

Preferably, each drive chain includes a phase shift algorithm.

Preferably, each drive chain includes a gain adjusting algorithm.

Preferably, a user or program selects the drive chain.

Preferably, the drive chain) is selected according to whether entrained gas is present in the flowing substance.

Preferably, the drive chain is selected according to the noise of the pick-off signals.

Preferably, the drive chain is selected by accessing a look up table that correlates a variety of conditions to particular drive chains.

According to another aspect of the present invention, a computer program product comprising computer usable medium including executable code for executing a process for generating a drive signal for a vibrating measuring device (5), the process comprising:

selecting a drive chain from at least two drive chains, wherein:

each drive chain modifies at least one pick-off signal to generate the drive signal;

each drive chain generates a different mode of vibration in the at least one conduit; and providing the drive signal generated by the selected drive chain to a drive.

Preferably, each drive chain modifies at least one pick-off signal in a manner that reinforces a particular drive frequency and suppresses other drive frequencies.

Preferably, each drive chain includes a filter that filters out undesired modes of vibration.

Preferably, each drive chain includes a phase shift algorithm.

Preferably, each drive chain includes a gain adjusting algorithm.

Preferably, a user or program selects the drive chain.

Preferably, the drive chain) is selected according to whether entrained gas is present in the flowing substance.

Preferably, the drive chain is selected according to the noise of the pick-off signals.

Preferably, the drive chain is selected by accessing a look up table that correlates a variety of conditions to particular drive chains.

DETAILED DESCRIPTION OF THE PRESENTLY PREFERRED EMBODIMENT

Figure 1:
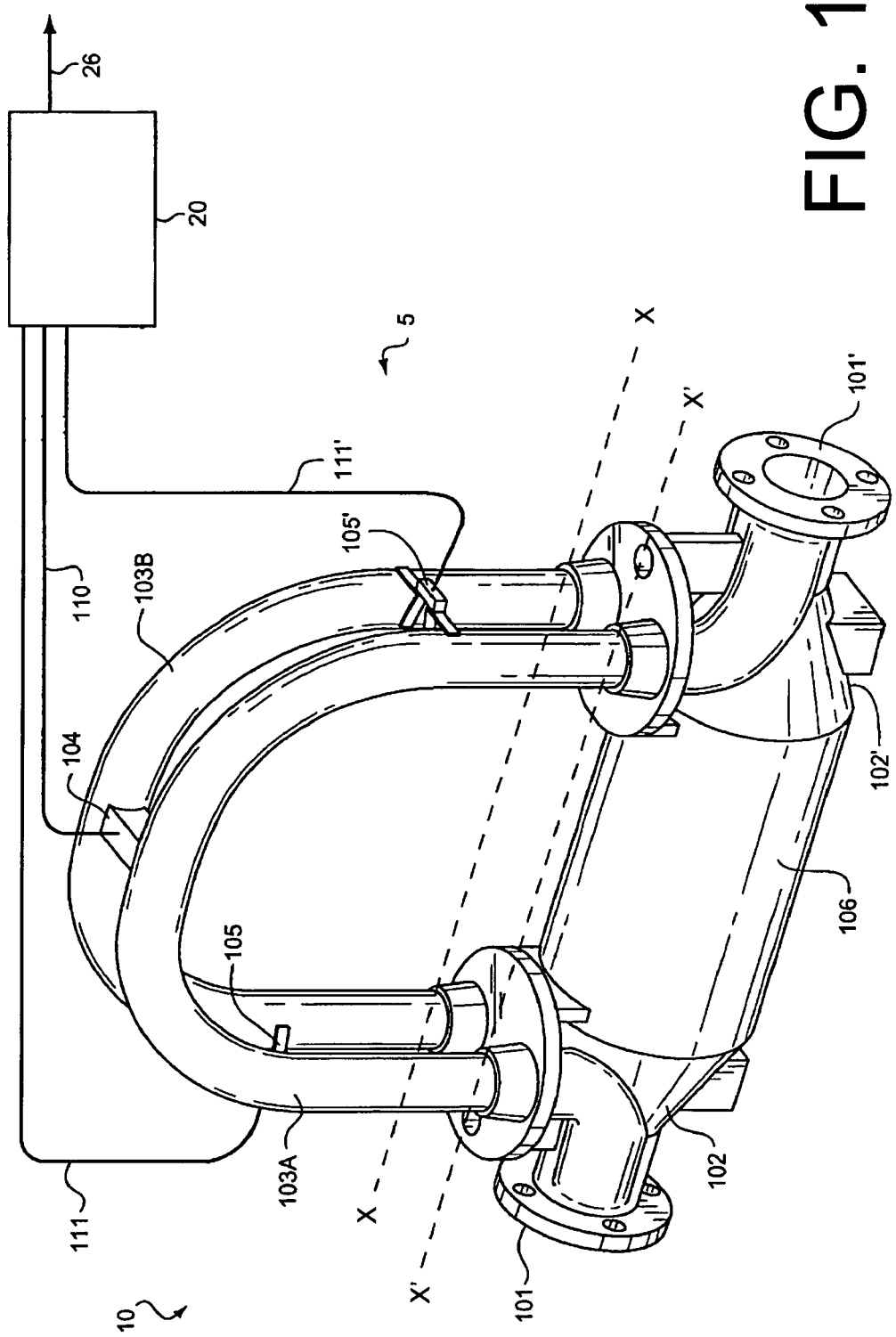
FIG. 1 depicts a perspective view of an example of a vibrating measuring device.

FIG. 1 illustrates an example of a vibrating measuring device 5 in the form of a Coriolis flow meter comprising a sensor assembly 10 and one or more electronics 20. The one or more electronics 20 are connected to sensor assembly 10 to measure a characteristic of a flowing substance, such as, for example, density, mass flow rate, volume flow rate, totalized mass flow, temperature, and other information.

The sensor assembly 10 includes a pair of flanges 101 and 101', manifolds 102 and 102', and conduits 103A and 103B. Manifolds 102, 102' are affixed to opposing ends of the conduits 103A, 103B. Flanges 101 and 101' of the present example are affixed to manifolds 102 and 102'. Manifolds 102 and 102' of the present example are affixed to opposite ends of spacer 106. Spacer 106 maintains the spacing between manifolds 102 and 102' in the present example to prevent undesired vibrations in conduits 103A and 103B. The conduits extend outwardly from the manifolds in an essentially parallel fashion. When sensor assembly 10 is inserted into a pipeline system (not shown) which carries the flowing substance, the substance enters sensor assembly 10 through flange 101, passes through inlet manifold 102 where the total amount of material is directed to enter conduits 103A and 103B, flows through conduits 103A and 103B and back into outlet manifold 102' where it exits the sensor assembly 10 through flange 101'.

The sensor assembly 10 of the present example includes a drive 104. The drive 104 is affixed to conduits 103A, 103B in a position where the drive 104 can vibrate the conduits 103A, 103B in the drive mode. More particularly, the drive 104 includes a first drive portion (not shown) affixed to conduit 103A and a second drive portion (not shown) affixed to conduit 103B. Drive 104 may comprise one of many well known arrangements, such as a first portion magnet mounted to conduit 103A and an opposing second portion coil mounted to conduit 103B.

In the present example, the drive mode is the first out of phase bending mode and the conduits 103A and 103B are preferably selected and appropriately mounted to inlet manifold 102 and outlet manifold 102' so as to provide a balanced system have substantially the same mass distribution, moments of inertia, and elastic modules about bending axes X-X and X'-X', respectively. In the present example, where the drive mode is the first out of phase bending mode, the conduits 103A and 103B are driven by drive 104 in opposite directions about their respective bending axes X and X'. A drive signal in the form of an alternating current is provided by one or more electronics 20, such as for example via pathway 110, and passed through the coil to cause both conduits 103A, 103B to oscillate.

Those of ordinary skill in the art will appreciate that other drive modes may be used within the scope of the present invention. By way of example, the drive mode may be a twist mode as described in U.S. Pat. No. 5,271,282, the disclosure of which is hereby incorporated herein by reference.

The sensor assembly 10 shown includes a pair of pick-offs 105, 105' that are affixed to conduits 103A, 103B. More particularly, first pick-off portions (not shown) are located on conduit 103A and second pick-off portions (not shown) are located on conduit 103B. In the embodiment depicted, the pick-offs 105, 105' are located at opposing ends of the conduits 103A, 103B. The pick-offs 105, 105' may be electromagnetic detectors, for example first pick-off portion magnets and second pick-off portion coils, that produce pick-off signals that represent the velocity and position of the conduits 103A, 103B. For example, the pick-offs 105, 105' may supply pick-off signals to the one or more electronics via pathways 111, 111'. Those of ordinary skill in the art will appreciate that the motion of the conduits 103A, 103B is proportional to certain characteristics of the flowing substance, for example, the mass flow rate and density of the material flowing through the conduits 103A, 103B.

In the example shown in FIG. 1, the one or more electronics 20 receive the pick-off signals from the pick-offs 105, 105'. Path 26 provides an input and an output means that allows one or more electronics 20 to interface with an operator. The one or more electronics 20 measure a characteristic of a flowing substance, such as, for example, density, mass flow rate, volume flow rate, totalized mass flow, temperature, and other information. More particularly, the one or more electronics 20 receive one or more signals, for example, from pick-offs 105, 105' and one or more temperature sensors (not shown), and use this information to measure a characteristic of a flowing substance, such as, for example, density, mass flow rate, volume flow rate, totalized mass flow, temperature, and other information.

The techniques by which vibrating measuring devices, such as, for example, Coriolis flow meters or densitometers, measure a characteristic of a flowing substance are well understood; see, for example, U.S. Pat. No. 6,505,131, the disclosure of which is hereby incorporated herein by reference; therefore, a detailed discussion is omitted for brevity of this description.

In the example shown in FIG. 1, the one or more electronics 20 provide a drive signal to the drive 104. More particularly, a drive chain, for example drive chains $C_1$, $C_2$, $C_3$, $C_N$, shown in the embodiment of FIG. 2, modifies one or more pick-off signals in a manner that reinforces the appropriate drive frequency and suppresses other drive frequencies. For example, a drive chain $C_1$ may modify the pick-off signal by filtering out non-desired modes, i.e. the modes of drive chains $C_2$, $C_3$, $C_N$, adjusting signal gain, and phase shifting the signal. After the drive chain modifies the one or more pick-off signals, the appropriate drive signal is sent to drive 105 in order to vibrate the conduits 103, 103'.

Those of ordinary skill in the art will appreciate that the drive chains of the present embodiment may be embodied in a software product, hardware, or a combination thereof. For example, the drive chains may include analogue hardware in the form of filters and software run processes, for example, one or more algorithms that phase shift the signal and adjust signal gain.

Figure 2:
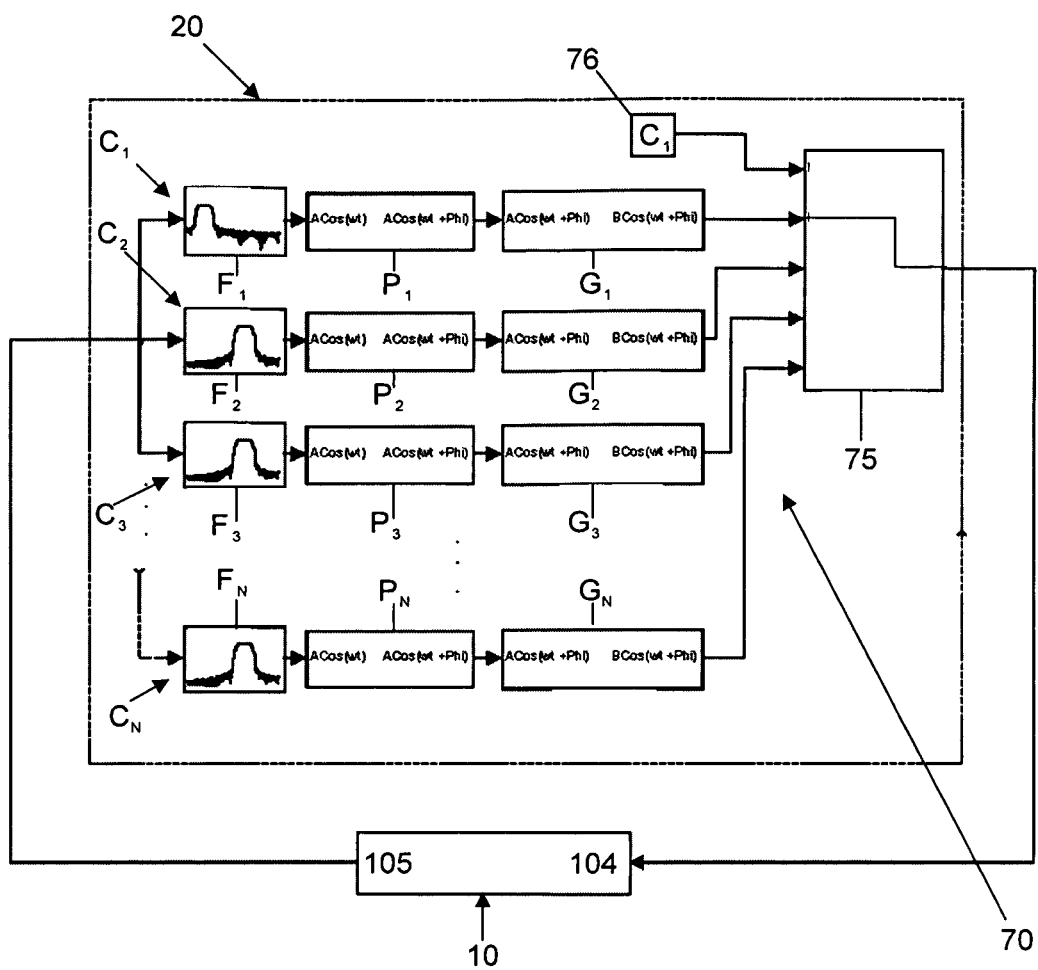
FIG. 2 depicts a perspective schematic view of a drive system including multiple drive chains.

Turning now to FIG. 2 an embodiment of a drive system 70 is shown that is capable selecting different drive chains. As shown in FIG. 2, the drive system 70 includes multiple drive chains, for example, drive chains $C_1$, $C_2$, $C_3$, and $C_N$. According to one aspect of the present embodiment, each drive chain, for example drive chains $C_1$, $C_2$, $C_3$, $C_N$, is configured to generate a different drive frequency or drive mode. According to another aspect of the present embodiment, each drive chain, for example, drive chains $C_1$, $C_2$, $C_3$, $C_N$, modifies one or more pick-off signals in a manner that reinforces the appropriate drive frequency of that drive chain. According to yet another aspect of the present embodiment, each drive chain, for example, drive chains $C_1$, $C_2$, $C_3$, $C_N$ modifies one or more pick-off signals in a manner that suppresses other drive frequencies, including other drive frequencies of other drive chains. By way of example, each drive chain $C_1$, $C_2$, $C_3$, $C_N$ may be provided with at least one filter $F_1$, $F_2$, $F_3$, $F_N$, for example an algorithm or hardware, at least one phase shift algorithm $P_1$, $P_2$, $P_3$, $P_N$, and at least one gain adjusting algorithm $G_1$, $G_2$, $G_3$, $G_N$ that modify one or more pick-off signals in the appropriate manner.

Those of ordinary skill in the art appreciate that the particular algorithms employed will depend on a number of factors. Furthermore, those of ordinary skill in the art will appreciate that in practice, vibrating measuring devices are generally not identical to each other. For example, and not limited to, vibrating measuring devices generally differ, at least to some extent, in their amount of mass, in their distribution of mass, in the vibration amplitudes and/or frequencies involved, and in the particular substance or density of the particular substance that flows through the conduit. Those of ordinary skill in the art will appreciate that even small differences in mass, distribution of mass, vibration amplitudes and/or frequencies, and in the particular substance or density of the particular substance that flows through the conduit will affect the particular drive chains and algorithms used. Accordingly, those of ordinary skill in the art will appreciate that certain routine testing may be required in order to determine the appropriate drive chains or algorithms for a particular vibrating measuring device.

As shown in FIG. 2, the drive system 70 includes a drive chain selector 75. According to one aspect of the present embodiment, the drive chain selector 75 is configured to allow selection of the appropriate drive chain, for example, drive chains $C_1$, $C_2$, $C_3$, $C_N$. Those of ordinary skill in the art will appreciate that the selector 75 of the present embodiment may be embodied in a software product, hardware, or a combination thereof. By way of example, the drive chain selector 75 may be a hardware switch and/or may be a software run process, for example, a process wherein a user or program selects or inputs, as at 76, the desired drive chain $C_1$, $C_2$, $C_3$, $C_N$, to be used.

Accordingly, in situations where a particular drive chain is unsuitable, a user or program may switch to a more suitable drive chain. For example, a particular drive chain may provide more accurate measurements in situations where entrained gas is present. By way of yet another example, a particular drive chain may generate pick-off signals have less noise, i.e. such that they occur at a frequency that differs from other frequencies that arise in the system. By way of still yet another example a program or user may access a look up table that correlates a variety of conditions to particular drive chains.

It should be apparent to those skilled in the art that it is within the scope of the present invention to use the principals discussed herein in conjunction with any type of vibrating measuring device, including, for example, densitometers, regardless of the number of drives, the number of pick-offs, the operating mode of vibration, or the determined characteristic of the flowing substance. The present description depicts specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. The detailed descriptions of the above embodiments are not exhaustive descriptions of all embodiments contemplated by the inventors to be within the scope of the invention.

Persons skilled in the art will recognize that certain elements of the above-described embodiments may variously be combined or eliminated to create further embodiments, and such further embodiments fall within the scope and teachings of the invention. It will also be apparent to those of ordinary skill in the art that the above-described embodiments may be combined in whole or in part to create additional embodiments within the scope and teachings of the invention.

Thus, although specific embodiments of, and examples for, the invention are described herein for illustrative purposes, various equivalent modifications are possible within the scope of the invention, as those skilled in the relevant art will recognize. The teachings provided herein may be applied to other embodiments than those described above and shown in the accompanying figures. Accordingly, the scope of the invention is determined from the following claims.

I claim:

1. A system for generating a drive signal in a vibrating measuring device (5), comprising:
   at least one conduit (103A) configured to receive a flowing substance;
   at least one drive (104) that vibrates the at least one conduit (103A);
   at least one pick-off (105) that measures motion of the at least one conduit (103A); and
   one or more electronics (20) configured to receive at least one pick-off signal from the at least one pick-off (105), with the one or more electronics (20) including at least two available drive chains ($C_1$, $C_2$, $C_3$, $C_N$), wherein
   each drive chain of the at least two available drive chains ($C_1$, $C_2$, $C_3$, $C_N$) modifies a pick-off signal to generate a drive signal including a different frequency and a different mode of vibration in the at least one conduit (103A);
   with the one or more electronics (20) being configured to select a drive chain from the at least two available drive chains ($C_1$, $C_2$, $C_3$, $C_N$), process the at least one pick-off signal with the selected drive chain to generate a drive signal, and provide the drive signal to the at least one drive (104).

2. The system for generating a drive signal in a vibrating measuring device (5) according to claim 1, wherein each drive chain ($C_1$, $C_2$, $C_3$, $C_N$) modifies at least one pick-off signal in a manner that reinforces a particular drive frequency and suppresses other drive frequencies.

3. The system for generating a drive signal in a vibrating measuring device (5) according to claim 1, wherein each drive chain ($C_1$, $C_2$, $C_3$, $C_N$) includes a filter that filters out undesired modes of vibration.

4. The system for generating a drive signal in a vibrating measuring device (5) according to claim 1, wherein each drive chain ($C_1$, $C_2$, $C_3$, $C_N$) includes a phase shift algorithm ($P_1$, $P_2$, $P_3$, $P_N$).

5. The system for generating a drive signal in a vibrating measuring device (5) according to claim 1, wherein each drive chain ($C_1$, $C_2$, $C_3$, $C_N$) includes a gain adjusting algorithm ($G_1$, $G_2$, $G_3$, $G_N$).

6. The system for generating a drive signal in a vibrating measuring device (5) according to claim 1, wherein a user or program selects the drive chain ($C_1$, $C_2$, $C_3$, $C_N$).

7. The system for generating a drive signal in a vibrating measuring device (5) according to claim 1, wherein the drive chain ($C_1$, $C_2$, $C_3$, $C_N$) is selected according to whether entrained gas is present in the flowing substance.

8. The system for generating a drive signal in a vibrating measuring device (5) according to claim 1, wherein the drive chain ($C_1$, $C_2$, $C_3$, $C_N$) is selected according to the noise of the pick-off signals.

9. The system for generating a drive signal in a vibrating measuring device (5) according to claim 1, wherein the drive chain ($C_1$, $C_2$, $C_3$, $C_N$) is selected by accessing a look up table that correlates a variety of conditions to particular drive chains ($C_1$, $C_2$, $C_3$, $C_N$).

10. A method for generating a drive signal for a vibrating measuring device (5), including at least one conduit (103A) configured to receive a flowing substance, at least one drive (104) that vibrates the at least one conduit (103A), at least one pick-off (105) that measures motion of the at least one conduit (103A), the method comprising the steps of:
    providing one or more electronics (20) configured to receive at least one pick-off signal from the at least one pick-off (105), with the one or more electronics (20) including at least two available drive chains ($C_1$, $C_2$, $C_3$, $C_N$), wherein
    each drive chain of the at least two available drive chains ($C_1$, $C_2$, $C_3$, $C_N$) modifies a pick-off signal to generate a drive signal including a different frequency and a different mode of vibration in the at least one conduit (103A);
    with the one or more electronics (20) being configured to select a drive chain from the at least two available drive chains ($C_1$, $C_2$, $C_3$, $C_N$), process the at least one pick-off signal with the selected drive chain to generate a drive signal, and provide the drive signal to the at least one drive (104).

11. The method for generating a drive signal in a vibrating measuring device (5) according to claim 10, wherein each drive chain ($C_1$, $C_2$, $C_3$, $C_N$) modifies at least one pick-off signal in a manner that reinforces a particular drive frequency and suppresses other drive frequencies.

12. The method for generating a drive signal in a vibrating measuring device (5) according to claim 10, wherein each drive chain ($C_1$, $C_2$, $C_3$, $C_N$) includes a filter that filters out undesired modes of vibration.

13. The method for generating a drive signal in a vibrating measuring device (5) according to claim 10, wherein each drive chain ($C_1$, $C_2$, $C_3$, $C_N$) includes a phase shift algorithm ($P_1$, $P_2$, $P_3$, $P_N$).

14. The method for generating a drive signal in a vibrating measuring device (5) according to claim 10, wherein each drive chain ($C_1$, $C_2$, $C_3$, $C_N$) includes a gain adjusting algorithm ($G_1$, $G_2$, $G_3$, $G_N$).

15. The method for generating a drive signal in a vibrating measuring device (5) according to claim 10, wherein a user or program selects the drive chain ($C_1, C_2, C_3, C_N$).

16. The method for generating a drive signal in a vibrating measuring device (5) according to claim 10, wherein the drive chain ($C_1, C_2, C_3, C_N$) is selected according to whether entrained gas is present in the flowing substance.

17. The method for generating a drive signal in a vibrating measuring device (5) according to claim 10, wherein the drive chain ($C_1, C_2, C_3, C_N$) is selected according to the noise of the pick-off signals.

18. The method for generating a drive signal in a vibrating measuring device (5) according to claim 10, wherein the drive chain ($C_1, C_2, C_3, C_N$) is selected by accessing a look up table that correlates a variety of conditions to particular drive chains ($C_1, C_2, C_3, C_N$).

19. A non-transitory computer readable medium containing computer instructions stored therein for executing a process for generating a drive signal for a vibrating measuring device (5), the process comprising the steps of:
  receiving at least one pick-off signal from at least one pick-off (105);
  selecting a drive chain ($C_1, C_2, C_3, C_N$) from at least two available drive chains ($C_1, C_2, C_3, C_N$), wherein
    each drive chain of the at least two available drive chains ($C_1, C_2, C_3, C_N$) modifies a pick-off signal to generate a drive signal including a different frequency and a different mode of vibration in the at least one conduit (103A);
  processing the at least one pick-off signal with the selected drive chain to generate a drive signal; and
  providing the drive signal to at least one drive (104).

20. The non-transitory computer readable medium according to claim 19, wherein each drive chain ($C_1, C_2, C_3, C_N$) modifies at least one pick-off signal in a manner that reinforces a particular drive frequency and suppresses other drive frequencies.

21. The non-transitory computer readable medium according to claim 19, wherein each drive chain ($C_1, C_2, C_3, C_N$) includes a filter that filters out undesired modes of vibration.

22. The non-transitory computer readable medium according to claim 19, wherein each drive chain ($C_1, C_2, C_3, C_N$) includes a phase shift algorithm ($P_1, P_2, P_3, P_N$).

23. The non-transitory computer readable medium according to claim 19, wherein each drive chain ($C_1, C_2, C_3, C_N$) includes a gain adjusting algorithm ($G_1, G_2, G_3, G_N$).

24. The non-transitory computer readable medium according to claim 19, wherein a user or program selects the drive chain ($C_1, C_2, C_3, C_N$).

25. The non-transitory computer readable medium according to claim 19, wherein the drive chain ($C_1, C_2, C_3, C_N$) is selected according to whether entrained gas is present in the flowing substance.

26. The non-transitory computer readable medium according to claim 19, wherein the drive chain ($C_1, C_2, C_3, C_N$) is selected according to the noise of the pick-off signals.

27. The non-transitory computer readable medium according to claim 19, wherein the drive chain ($C_1, C_2, C_3, C_N$) is selected by accessing a look up table that correlates a variety of conditions to particular drive chains ($C_1, C_2, C_3, C_N$).

* * * * *